United States Patent
Zeidell et al.

(10) Patent No.: US 12,194,314 B2
(45) Date of Patent: Jan. 14, 2025

(54) RADIATION DOSIMETERS AND APPLICATIONS THEREOF

(71) Applicant: WAKE FOREST UNIVERSITY, Winston-Salem, NC (US)

(72) Inventors: Andrew Zeidell, Winston-Salem, NC (US); Oana D. Jurchescu, Winston-Salem, NC (US); J. Daniel Bourland, Winston-Salem, NC (US); Tong Ren, Winston-Salem, NC (US)

(73) Assignee: WAKE FOREST UNIVERSITY, Winston-Salem, NC (US)

( * ) Notice: Subject to any disclaimer, the term of this patent is extended or adjusted under 35 U.S.C. 154(b) by 713 days.

(21) Appl. No.: 17/365,438

(22) Filed: Jul. 1, 2021

(65) Prior Publication Data
US 2022/0001208 A1    Jan. 6, 2022

Related U.S. Application Data

(60) Provisional application No. 63/048,483, filed on Jul. 6, 2020.

(51) Int. Cl.
*A61N 5/10* (2006.01)
*G01T 1/02* (2006.01)

(52) U.S. Cl.
CPC ............ *A61N 5/1071* (2013.01); *G01T 1/026* (2013.01)

(58) Field of Classification Search
None
See application file for complete search history.

(56) References Cited

U.S. PATENT DOCUMENTS

2011/0089959 A1* 4/2011 Raval ............... H10K 39/36
324/702
2016/0187495 A1* 6/2016 Scott ................ H01L 31/119
250/370.07
2019/0162863 A1* 5/2019 Syme ............... H10K 30/80

* cited by examiner

*Primary Examiner* — Marcus H Taningco
(74) *Attorney, Agent, or Firm* — J. Clinton Wimbish; Maynard Nexsen PC (57) ABSTRACT

In one aspect, radiation dosimeters are described herein comprising organic field effect transistors. Briefly, a radiation dosimeter comprises an organic field effect transistor having composition and/or electronic structure exhibiting a shift in threshold voltage as a function of radiation dose.

19 Claims, 5 Drawing Sheets

RADIATION DOSIMETERS AND APPLICATIONS THEREOF

RELATED APPLICATION DATA

The present invention claims priority pursuant to 35 U.S.C. § 119(e) to U.S. Provisional Patent Application Ser. No. 63/048,483 filed Jul. 6, 2020 which is incorporated herein by reference in its entirety.

STATEMENT OF GOVERNMENT RIGHTS

This invention was made with government support under Grant Nos. DMR-1627925 and ECCS-1810273 awarded by the National Science Foundation (NSF). The government has certain rights in the invention.

FIELD

The present application relates to radiation dosimeters and, in particular, to radiation dosimeters comprising organic field effect transistors.

BACKGROUND

Cancer is one of the most common causes of death, with alarming growth rates worldwide, but fortunately can be treated with early diagnosis and care. Over the past decades, heroic research efforts focused on elucidating the causes and developing effective treatments for this disease, with chemotherapy, radiation therapy and surgery emerging as the leading approaches for treating cancer patients. In radiation therapy, one of the most common procedures, high-energy ionizing photon and electron radiation is used to destroy or reduce the growth of cancer cells. Most modern treatment systems utilize linear accelerators to generate beams of electrons or x-rays in the megavoltage (MV) range, radioisotopes that produce gamma rays, or more recently, cyclotrons to produce high energy protons.

One of the biggest challenges in radiation oncology is to deliver the radiation only to the regions were the malignant cells are located, since the ionizing radiation can also injure healthy tissues surrounding the target volumes. Many techniques have been implemented for maximizing the target dose, while minimizing normal tissue dose—this balance is always considered when planning a patient's radiation regimen. Radiation treatment regimens include high-dose single fraction (eg, stereotactic radiosurgery (SRS)), hypofractionated (stereotactic body radiation treatment (SBRT)), and conventional fractionated (3D conformal radiation treatment (3D-CRT), intensity modulated radiation treatment (IMRT)) techniques that encompass considerations for physical and biological optimization criteria. Being able to measure the absorbed dose with high accuracy and sensitivity is therefore critical to successful patient treatment and long-term survival. In contemporary clinical routines, first the beam is shaped, and the dose distribution is measured using a cylindrical diode array inside a poly-methyl methacrylate (PMMA) phantom and then compared to the calculated dose distribution from a planning system, a quality assurance process that takes place a priori, during a treatment planning phase. Modern computers and machine learning techniques aid technicians in estimating the dose distribution within the patient by accounting for differences in geometry and composition between the patient and the detector, but unfortunately uncertainties persist. In addition, positioning of the patient and even minor movements (e.g. breathing), can alter the received dose and targeted volume, and thus affect the outcome of the procedure. During the therapy session, electronic portal imaging devices (EPIDs) are used to ensure accurate beam placement, but the large number of variables involved in the post-processing of the data can result in significant errors in the approximated dose profile in a patient's body due to inhomogeneities in the target (muscles/bones/adipose tissue), and person-to person variations in the patient's anatomic structures.

SUMMARY

In view of the foregoing, radiation dosimeters are described herein comprising organic field effect transistors. Briefly, a radiation dosimeter comprises an organic field effect transistor having composition and/or electronic structure exhibiting a shift in threshold voltage as a function of radiation dose.

In another aspect, methods of measuring doses of radiation administered to a patient are described herein. In some embodiments, a method comprises positioning a radiation dosimeter over a target area for the radiation dose, the radiation dosimeter comprising an organic field effect transistor having composition and/or electronic structure exhibiting a shift in threshold voltage as a function of radiation dose, passing the radiation dose through the radiation dosimeter to tissue of the target area, and quantifying the dose of radiation from the shift in the threshold voltage of the organic field effect transistor in response to receiving the dose of radiation.

These and other embodiments are further described in the following detailed description.

DETAILED DESCRIPTION

Embodiments described herein can be understood more readily by reference to the following detailed description and examples and their previous and following descriptions. Elements and apparatus described herein, however, are not limited to the specific embodiments presented in the detailed description. It should be recognized that these embodiments are merely illustrative of the principles of the present invention. Numerous modifications and adaptations will be readily apparent to those of skill in the art without departing from the spirit and scope of the invention.

Figure 1A:
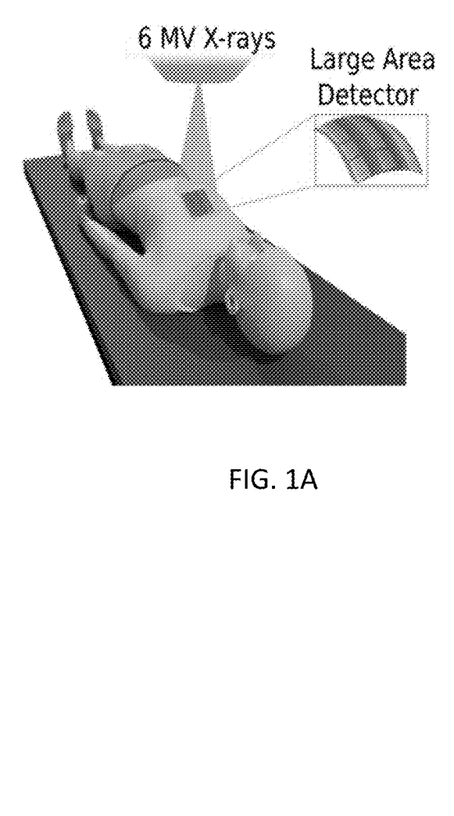
FIG. 1A illustrates placement of the RAD-OFET on patients during radiation therapy, according to some embodiments.
Figure 1B:
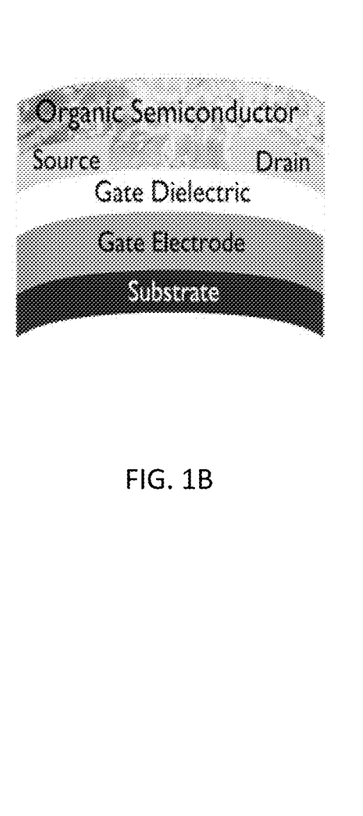
FIG. 1B illustrates architecture of an individual RAD-OFET sensing element, according to some embodiments.
Figure 1C:
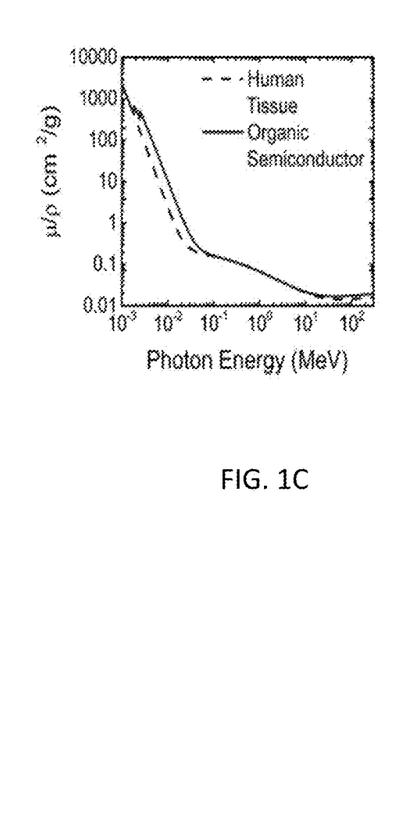
FIG. 1C is a comparison of the mass attenuation coefficient for human tissue and organic semiconductor over the large range of photon energies used for imaging and cancer treatment.

As illustrated in FIG. 1a, radiation dosimeteres described herein can be plased directly at the point where the radiation interacts with the human body. This approach will greatly enhance the accuracy of the measurements by eliminating the need for extensive data processing. At the same time, it will reduce the complexity and cost of the instruments and, therefore, the treatment. Here, we report on such radiation dosimeters based on organic field-effect transistors (OFETs), called the RAD-OFETs (RAdiation Detector based on Organic Field-Effect Transistors). These detectors take advantage of the key properties of organic semiconductors (OSCs): they are lightweight, conformal to the curvature of the human skin surface (FIG. 1b), and thin enough to be placed at the site of irradiation without disturbing the delivered dose. The similarity in the density of organic compounds and human tissue, given by the comparable atomic numbers (Z) (FIG. 1c), minimizes the correction factor for estimating the dose applied to the patient, especially for megavoltage photon energies.

We obtain sensitivities as high as $2.2 \cdot 10^7 \pm 0.2 \cdot 10^7$ µC $Gy^{-1}$ $cm^{-3}$ (60 mV/cGy) by monitoring the shift in the OFET threshold voltage and propose a model that describes the physical mechanism responsible for the observed changes. The model is based on photogeneration of charges upon x-ray exposure, followed by a distinct response to interaction with radiation of the electrons and hole, respectively. We find that the electron trapping at the semiconductor/dielectric interface occurs regardless of the absorbed dose. On the contrary, the dynamics of hole transport is given by the accumulation due to photoelectric effect and trapping by defects generated in the organic semiconductor crystal, a process which is dependent on the radiation dose. Sensitivities up to $5.2 \cdot 10^7 \pm 0.3 \cdot 10^7$ µC $Gy^{-1}$ $cm^{-3}$ were demonstrated in RAD-OFETs fabricated on flexible substrates, with an exceptional robustness upon bending. Our medical x-ray dosimeters could offer high sensitivity and ease of operation, while also taking advantage of the simple processing of organic materials, where large-area arrays can be easily fabricated on flexible substrates by printing, spray-coating or other roll-to-roll manufacturing techniques. These results provide a simple, effective and cost-efficient solution for detection of ionizing radiation, which may yield new products for medical diagnostics and treatment dose measurement using low-cost large area portable or wearable detectors. The versatile chemistry of organic compounds allows for fine tuning of Z by modifications in the molecular structure to finely match the Z of any target material, whether it be bone, fat (adipose) tissue, or muscle tissue, therefore making this technique suitable for dose monitoring during imaging and treatment of a wide variety of medical radiation procedures for kilovoltage and megavoltage photons. These results uncover new opportunities for organic circuits that will not only improve the quality of healthcare through better, lower cost in vivo dose monitoring during radiation therapy, but can also have applications into portable and wearable detectors or high energy radiation detectors for defense and space applications.

Organic semiconductors have drawn considerable attention in the medical field due to their inherent versatility in molecular design, their ease of processing, and biocompatibility. Devices made from OSCs can withstand temperatures used in sterilization, are stable in aqueous environments, and have been included in applications like heart rate monitors, and large area imaging arrays, all on biocompatible substrates. The use of biocompatible substrates has enabled ultra-lightweight sensors for bio-interfacing, from sensors thin enough to be attached directly to heart tissues to act as an electro-cardiogram, to neural probes capable of controlling neurotransmitter delivery. Novel device design has also opened up pathways to electrochemical devices, which can be used to sense metabolites produced in the body and act as bio-powered sensors operating off electrochemical reactions with human skin to sense glucose and peptides.

Radiation detection using organic materials is a developing area, with applications ranging from hazardous material identification and homeland security, to imaging, personnel safety or space applications. Much of this work, however, has focused on high radiation doses, or charged particle detection. Here we focus on radiation doses between 0.1 Gy and 10 Gy (Gy=J $kg^{-1}$), which are typical values for medical imaging and therapy: for example doses of 0.0005 cGy account for dental and limb x-ray imaging, 0.01 to 0.2 cGy are used for torso imaging, 0.4 to 2 cGy for body CT scans, 2.5 cGy for positron emission tomography (PET) scans, while radiation treatment of tumors requires doses between 100 to 200 cGy per fraction. To the best of our knowledge, this is the first example of using organic thin-film devices as dosimeters for radiation procedures used for cancer diagnosis and treatment.

OFETs Response to X-Ray Irradiation—Passive Dosimeters, i.e. RAD-OFETs

The organic field-effect transistors used in this work had a bottom-gate, bottom contact geometry. This device architecture allows for direct exposure of the organic semiconductor to the radiation beam. We started with a rigid structure, with a $SiO_2$ layer playing the role of bottom-gate dielectric, and later expanded to large-area flexible substrates with a Cytop gate dielectric. The contacts were made of Au and the semiconductor was 2,8-difluoro-5,11-bis (triethylsilylethynyl)anthradithiophene (diF-TES-ADT), a material that has shown remarkable electrical properties, with charge carrier mobilities close to 20 $cm^2$ $V^{-1}$ $s^{-1}$ in devices with near ideal current-voltage characteristics, and strong sensitivity to x-rays, although past work has focused on much higher doses and used different methods for detection. Other small molecule semiconductors are also possible, including those listed in Table I.

TABLE I

Figure 2A:
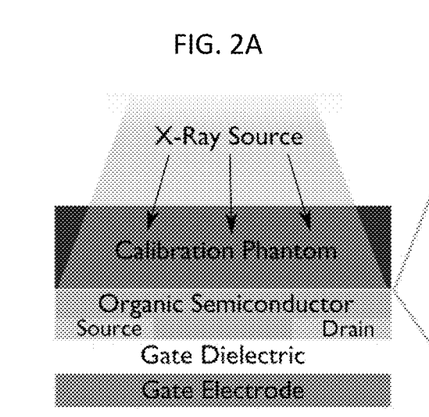
FIG. 2A is an illustration of an experimental setup, wherein the 1.5 cm thick tissue equivalent phantom slab above the OFET ensures the calibrated dose of FIG. 2B is delivered to devices during the experiment.
Figure 2B:
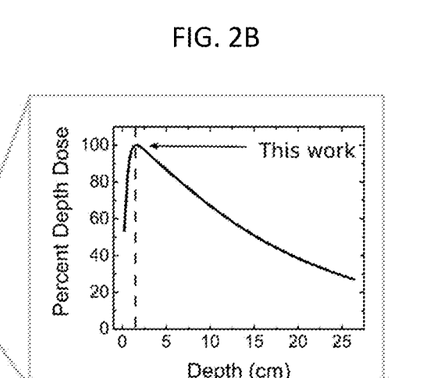
FIG. 2B illustrates radiation dosage according to some embodiments.

Small Molecule Semiconductor diF-TES-ADT
diF-TIPS-ADT
diF-TEG ADT
TES-ADT
TIPS Pn
F2 TIPS Pn
F4 TIPS Pn
F8 TIPS Pn
2,8-difluoro-5,11-bis(tri-sec-butylsilylethynyl) pentacenedithiophene
2,8-difluoro-5,11-bis(tri-sec-butylsilylethynyl) tetracenedithiophene The OFETs were fabricated using standard procedures and their electrical properties were first characterized in air and dark, prior to exposure. The devices were sandwiched without compression between two slabs of tissue equivalent calibration layers and irradiated through the layer. The experimental set-up is shown in FIG. 2a. The x-ray radiation was supplied by a medical-grade linear accelerator (Elekta Versa HD™, Wake Forest University Baptist Medical Center), with the corresponding relative dose as a function of depth as shown in FIG. 2b. Test samples consisting of arrays of OFET devices were placed in the center of the x-ray field, as described in the Methods section. This setup reproduces the reference irradiation geometry used for radiation beam calibration in the clinical setting. The samples were exposed to radiation doses in increments of 0.2 Gy between 0 and 1 Gy, and in increments of 2 Gy from 2 to 10 Gy, at a nominal dose rate of 6 Gy min$^{-1}$. Control samples were fabricated using identical procedures, but were not exposed to x-rays, and were tested along with the irradiated ones, to be able to decouple the aging effects from the interaction with radiation.

Figure 2C:
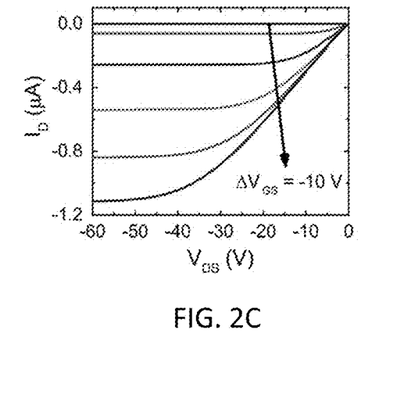
FIG. 2C illustrates typical I-V characteristics of an OFET.
Figure 2D:
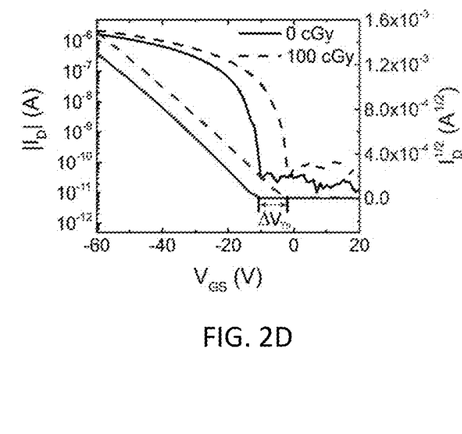
FIG. 2D is an example of the threshold voltage shift induced by radiation exposure, according to some embodiments.

Typical device output characteristics are shown in FIG. 2c, where we plot the drain current $I_D$ as a function of source-drain voltage $V_{DS}$ for fixed source-gate voltages, $V_{GS}$. In FIG. 2d we show the dependence of $I_D$ on $V_{GS}$ at constant $V_{DS}$ before exposure to radiation (solid line) and after absorbing 100 cGy of radiation (dashed line); the curves obtained after other exposure doses are also available. It can be clearly observed that irradiation caused a shift in the threshold voltage of the OFET, i.e. the intercept of the square root of the $I_D$ curve (blue) and the $V_{GS}$-axis, as marked in FIG. 2d. This shift $\Delta V_{Th}$ is described by Equation 1:

$$\Delta V_{Th} = V_{Th_D} - V_{Th_0} \quad (1)$$

where $V_{Th_D}$ represents the threshold voltage at the target dose and $V_{Th_0}$ the threshold voltage at zero dose. To ensure that the threshold voltage was uniformly determined for each measurement, we adopted the method of the second derivative of $I_D$ with respect to $V_{GS}$. This type of dosimetry, where the measurements are taken after exposing the sample to radiation, is referred to as passive. Passive sensors rely on the detection of changes induced in the sample upon exposure to radiation and that persist after exposure; on the contrary, active sensors monitor in real time by recording the photoconductive gain.

Figure 3A:
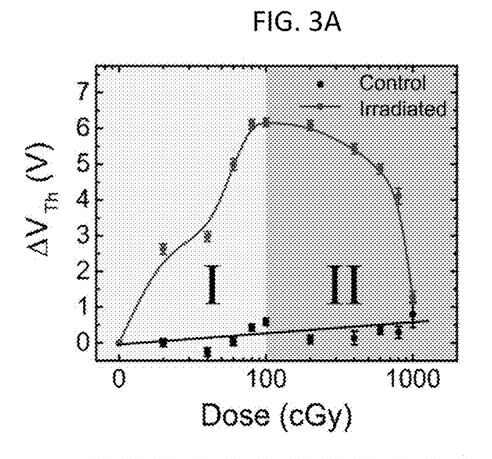
FIG. 3A illustrates a threshold voltage shift versus applied radiation dose for irradiated samples (circles) and the control devices (squares). In region I the shift is positive, while in region II the shift is negative for the irradiated sample. No significant changes were recorded for the control sample.

In FIG. 3a we plot the shift in the threshold voltage as a function of radiation dose, in red, along with the changes recorded in the control sample. While the control samples exhibit negligible changes, a shift in the threshold voltage can be observed upon irradiation, with two regions being clearly distinguished. At low irradiation doses, Region I—between 0 to 1 Gy, the irradiated OFETs exhibited a positive shift in the threshold voltage, up to a value of 6.1±0.2 V, obtained at 1 Gy. The average sensitivity of the detector, defined as $S_V = \Delta V_{Th}/\text{Dose}$, was determined to be $S_V = 60 \pm 8$ mV cGy$^{-1}$ for region I, a value which corresponds to $S_I = 2.2 \cdot 10^7 \pm 0.2 \cdot 10^7$ µC Gy$^{-1}$ cm$^{-3}$, where $S_I = (I-I_0)/(\text{Detector Volume} \cdot \text{Dose Rate})$, I is the current measured after exposure, and $I_0$ is the current prior to irradiation (both currents correspond to an applied gate voltage of $V_{GS} = -60$V). This sensitivity value is similar to that obtained at high doses with other dosimeters based on organic semiconductors, but in our case the performance was obtained under clinically relevant conditions for radiation treatment, where typical doses applied to patients do not exceed 200 cGy per treatment. In Region II, from 1 to 10 Gy, a negative shift in the threshold voltage is observed, with a sensitivity of $S_V = 4.6 \pm 0.9$ mV cGy$^{-1}$ ($S_I = 8.9 \cdot 10^6 \pm 0.2 \cdot 10^6$ µC Gy$^{-1}$ cm$^{-3}$).

Figure 3B:
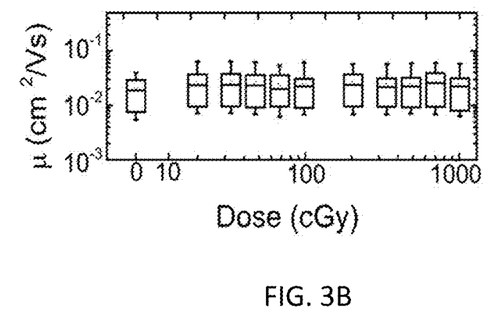
FIG. 3B is a box plot showing that the charge carrier mobility remains unchanged as a function of dose.
Figure 3C:
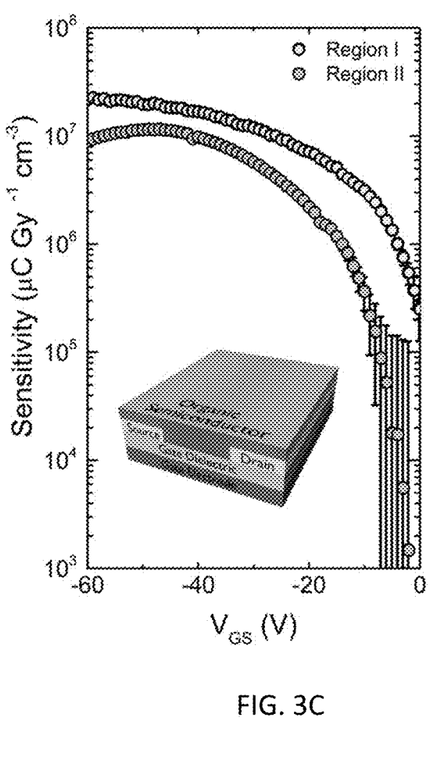
FIG. 3C illustrates average device sensitivity as a function of gate voltage in the two dose regimes, according to some embodiments.

To gain more insights into the processes responsible for the observed voltage shifts, we also evaluated the evolution of the charge carrier mobility (µ), in response to sample irradiation. The mobility was calculated from the slope of the square-root of the drain current with respect to the gate-source voltage (blue curves in FIG. 2d), using Equation 2:

$$I_D = \frac{W}{L} \frac{C_i}{2} \mu (V_{GS} - V_{Th})^2 \quad (2)$$

where L and W are the channel length and the channel width, respectively, and $C_i$ the capacitance per unit area of the dielectric. FIG. 3b shows the response of µ to cumulative dose; it is notable that the mobility did not change over the course of the treatments, suggesting that the organic semiconductor layer does not experience major chemical changes. Indeed, nuclear magnetic resonance, gas chromatography, UV-Vis, and thin-layer chromatography indicated that no degradation occurs in the organic semiconductor film. We do not exclude, however, that chemical changes take place, but the resulting impurity is below the detection limit of our techniques. Attempts to restore the device properties by thermal annealing or room-temperature annealing resulted in partial recovery, while the solvent annealing results were inconclusive. The evolution of sensitivity with the gate voltage for the low and high dose rates is included in FIG. 3c in yellow and blue, respectively. At low bias the sensitivity is hampered by multiple trapping and de-trapping events, which also impact the accuracy of reading, as demonstrated by the large error bars. When the voltage exceeds a critical value, which allows the majority accumulated charge carriers to be free, only a small dependence of voltage is recorded, thus the RAD-OFET response is independent on the applied voltage.

Physical Model for OFET Dosimeter Operation

Figure 4A:
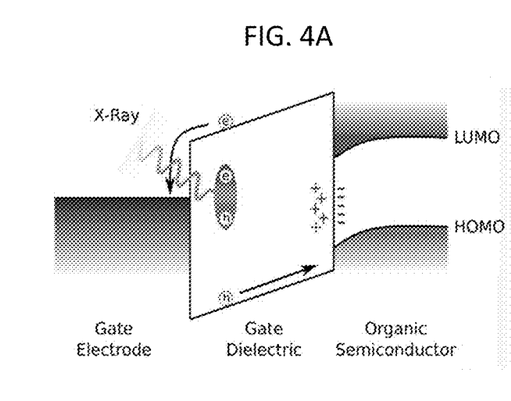
FIG. 4A provides band energy diagram illustrating the generation of electron-hole pairs when the device is irradiated, and the accumulation of deeply trapped holes at the interface, according to some embodiments.
Figure 4B:
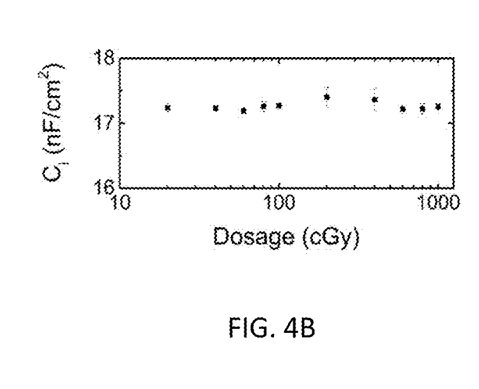
FIG. 4B illustrates capacitance measurements of the dielectric suggesting that holes are not trapped in the bulk of the dielectric.

The experimental results obtained upon controlled x-ray irradiation of the OFETs allowed us to propose a mechanism for the operation of the proposed dosimeters. The invariance in charge carrier mobility, along with partial recovery upon annealing, encouraged us to consider interfacial effects and structural defects as possible causes for the observed changes. The positive threshold voltage shift recorded upon exposure to low dose rates (Regime I) is indicative of electron trapping, a phenomenon that can occur either in the dielectric or in the organic semiconductor close to the semiconductor/dielectric interface. The interaction of x-rays with the OFETs results in a cascade of events. First, ionizing radiation causes the formation of an electron-hole pair, i.e. an exciton, in the organic semiconductor and in the $SiO_2$ layers (see FIG. 4a). A fraction of these photogenerated charges will immediately recombine, while the rest will dissociate, resulting in free electrons and holes. The electrons are trapped at the gate dielectric by hydroxyl groups or other impurities and defects present here, while the holes, which are more resilient to trapping events, contribute directly to transport. There will be two contributions to the hole density: one from the processes occurring within the organic semiconductor layer, and the other from the dielectric, where the holes move through a series of hopping states towards the dielectric semiconductor interface to contribute to transport (FIG. 4a). The effect can be reduced if a high density of holes remains trapped in the oxide, a process that would contribute to a negative shift in the threshold voltage, which counteracts the effect of the holes that migrate to the interface and contribute to a positive shift. By performing capacitance measurements on the dielectric layer (FIG. 4b), we concluded that the hole trapping in the oxide is minimal, since the dielectric capacitance remained constant at the dose levels used in this study. Some of the holes that reach the interface may, however, become deeply trapped here, creating long-lived states which persist over longer time scales (e.g. days, months) and contribute to a negative shift in threshold voltage. While in Region I the photogeneration of holes overcomes the trapping events, resulting in a shift towards more positive threshold voltages, the higher doses (>100 Gy) experienced by the OFETs in Regime II appear to generate significant trapping and lead to a negative shift. This shift results from the eventual build-up of deeply trapped holes at the interface and the structural defects occurring in the semiconductor, although we do not exclude the possibility of material degradation at levels below the detection limit of our chemical analysis techniques, but that are relevant to electronic transport.

Figure 4C:
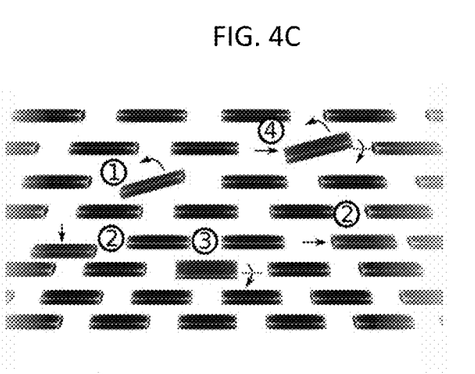
FIG. 4C is an illustration of position disorder in the diF-TES-ADT lattice, rotation (1,3), translation (2), or a mixture (4), according to some embodiments.
Figure 4D:
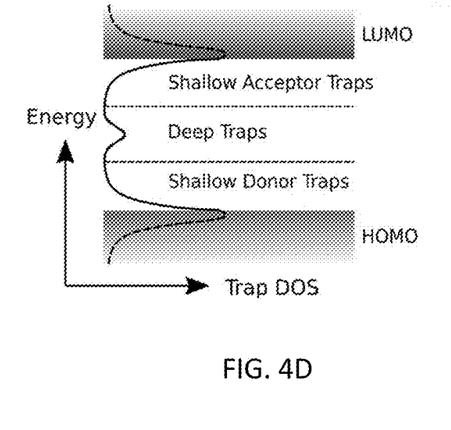
FIG. 4D illustrates the density of states in the band gap, energetically distinguishing deep from shallow traps.

Trap generation in organic materials upon interaction with ionizing radiation has sparked great interest lately. Batlogg and coworkers showed that proton irradiation results in cleaving of the C—H bond in single crystal rubrene, a process that generates deep trap states. They also found that x-ray irradiation yields local structural disorder, which is a common source of traps in organic semiconductors. Proton irradiation of triisopropylsilyl ethynyl (TIPS) pentacene OFETs resulted in positional disorder, and electron irradiation of rubrene thin films induced n-doping and a negative threshold voltage shift. Podzorov and coworkers used air-gap rubrene OFETs to eliminate the interfacial affects and concluded that the shifts recorded in the threshold voltage upon interaction with x-rays result from the deep traps created in the crystal. FIG. 4c includes a sketch of possible molecular re-orientations leading to positional disorder in the diF-TES-ADT film. The solid-state packing was elucidated in our past work, and the distortion is exaggerated here for clarity: it includes rotations (1, 3), translations (2), and a combination of both (4). Such defects have been shown to be the origin of electronic traps with an energetic distribution that is dependent on the material and the exact nature of the defect. A schematic representation of the energetic distribution of the trap density of states is included in FIG. 4d, with shallow traps creating acceptor-like and donor-like tail states in the vicinity of the frontier orbitals and deep traps laying in the middle of the band gap. Since we have not observed changes in charge carrier mobility upon exposure to radiation (FIG. 3b), we hypothesize that the molecular re-arrangements generate deep traps. De-trapping of charge carriers residing here is highly unlikely since the trap depth is high, and thus they cannot contribute to transport.

RAD-OFETs for Large-Area Conformal Electronics

Figure 5A:
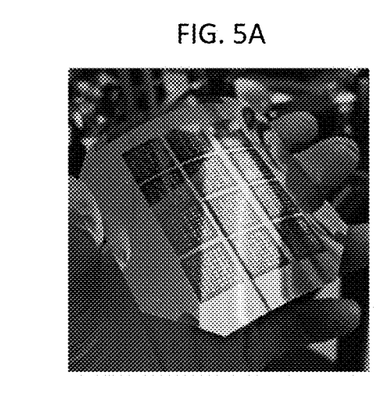
FIG. 5A illustrates an array of diF-TES-ADT OFET devices on PET/ITO substrates.
Figure 5B:
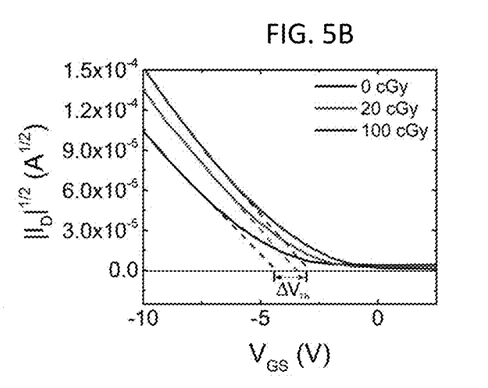
FIG. 5B provides square root of $I_D$ versus $V_{GS}$ illustrating the shift in threshold voltages as a function of dose, according to some embodiments.
Figure 5C:
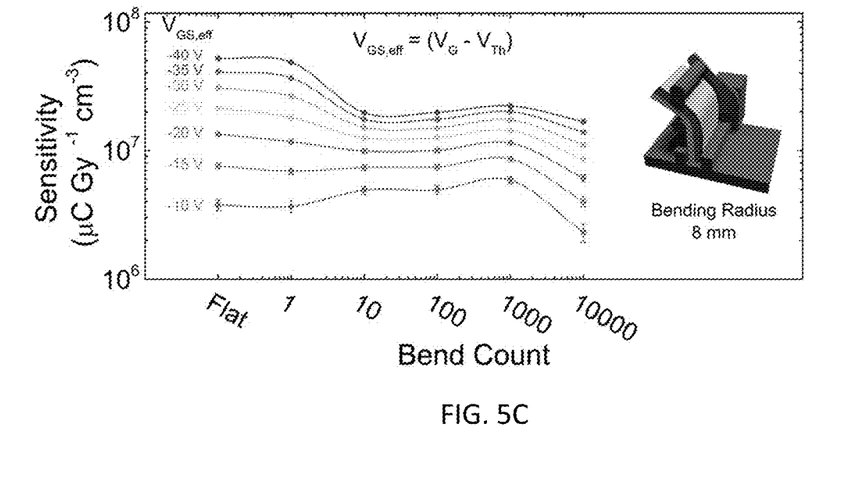
FIG. 5C illustrates RAD-OFET sensitivity after repeating bending cycles, for different effective $V_{GS}$. The inset shows a schematic of the computer-controlled bending set-up.

The tests performed on samples fabricated on $SiO_2$ provide robust perspectives for OFET adoption in medical radiation dosimetry. To take full advantage of the unique properties of organic semiconductors, next we integrated them with flexible substrates. Large-area, flexible dosimeters can be placed directly onto the patient without the need for additional hardware, allowing for a higher accuracy and resolution of radiation detection and reducing the complexity and cost of the medical equipment. These devices were fabricated in a bottom gate, bottom contact configuration, onto polyethylene terephthalate (PET) flexible substrates with a predefined indium tin oxide (ITO) layer, which played the role of the gate electrode, and Cytop gate dielectric (FIG. 5a). Due to the hydrophobic nature of the fluorinated polymer Cytop, an additional surface treatment was applied to increase its surface energy and allow solution deposition of the organic semiconductor, as described elsewhere. These devices exhibited similar shifts in the threshold voltage, but the magnitude of this shift was smaller. To test the mechanical robustness of the flexible OFET dosimeter, devices were flexed using a computer-controlled servo (FIG. 5c, inset) to a bending radius of 8 mm. Devices were exposed to a dose of 100 cGy and the sensitivity was measured as a function of the number of folding and unfolding cycles; the results for different effective gate voltages are included in FIG. 5, where the effective gate voltage is the difference between the applied gate voltage and the device threshold voltage $V_{GS,eff} = V_{GS} - V_{Th}$. The dependence of sensitivity on gate voltage is in agreement with the results presented in FIG. 3c. As for the tolerance to bending, a slight decrease in sensitivity occurs after 10 bends, most likely due to mechanical strains created at device interfaces and partial layer delamination, followed by a region of constant response between 10 and 10,000 bending cycles. A drastic decrease in sensitivity is observed after 10,000 cycles. Optical inspection of the films suggests that the micro-cracks that formed in the film are responsible for the performance degradation. Nevertheless, the good tolerance to folding exhibited by our OFET radiation detectors for the first 1000 bending cycles makes them attractive for incorporation in large area flexible radiation detectors.

Discussion

We introduced a new concept for fabricating passive radiation dosimeters for medical applications, which we named the RAD-OFET. The device is based on organic thin-film transistors, and the radiation dose is detected as a shift in the threshold voltage. The sensor is robust and highly sensitive for doses relevant to a variety of medical radiation procedures, including patient dose monitoring during cancer diagnosis and therapy. To understand the results, we proposed a model based on photogeneration of charges upon x-ray exposure, followed by charge trapping at the semiconductor/dielectric interface. The hole dynamics is governed by a competition between the accumulation of the photo-generated holes and deep trapping within the organic semiconductor, a process which is highly depended on the radiation dose. At low doses, below 200 cGy, trapping is minimal, and a positive shift is recorded in the threshold voltage, with a sensitivity of $60 \pm 8$ mV $cGy^{-1}$ ($2.2 \cdot 10^7 \pm 0.2 \cdot 10^7$ µC $Gy^{-1}$ $cm^{-3}$). At high doses the trap formation prevails, leading to a negative shift and a sensitivity of 4.6±0.9 mV cGy$^{-1}$ (8.9·10$^6$±0.2·10$^6$ μC Gy$^{-1}$ cm$^{-3}$). Solution processing allowed for integration with flexible substrates for the development of conformal electronics. Placement of the sensor directly onto the human body, coupled with the similarity in the Z-number between the electronically active layer and the human tissue, may greatly enhance the precision and reduce the complexity of the medical equipment, facilitating high quality measurement of patient doses. The application of therapeutic radiation with high precision increases the effectiveness on treating cancerous tissue and minimizes the impact on the surrounding healthy cells. The sensitivity of the proposed devices can be further enhanced with fine tuning the molecular structure of the organic semiconductor layer. These findings uncover new opportunities for organic circuits that will not only improve the quality of patient care, but they can have applications even beyond the cancer therapy. Such applications include OFET dosimeter placement in unique irradiation geometries and types, monitoring of personnel dose in hazardous environments, and measurement of space radiation.

Materials and Methods

Device Fabrication. Bottom-gate, bottom-contact devices were fabricated on both highly doped silicon substrates with a 200 nm SiO$_2$ dielectric layer, and PET/ITO substrates with a protein-modified dielectric layer, as described in earlier work. The SiO$_2$ substrates were cleaned by immersion in hot acetone (85° C.) for ten minutes, followed by a thorough rinse in acetone and immersion in hot isopropyl alcohol (IPA, 85° C.) for ten minutes. The substrates were then rinsed in IPA and dried by a stream of nitrogen. Next, they were exposed to a UV-Ozone treatment for 10 minutes, rinsed in deionized water, and dried in a nitrogen stream. For both substrate types, the source and drain electrodes were patterned by shadow mask, and consisted of a 5 nm titanium adhesion layer deposited by electron beam deposition at a rate of 1 Å/s, followed by thermally evaporated gold at a rate of 0.5 Å/s. The contacts were then treated for 30 minutes using a 30 mM solution of room-temperature pentafluorobenzene thiol (PFBT) in ethanol, rinsed with ethanol, and dried in a stream of nitrogen. The diF-TES-ADT semiconductor film was deposited by spin coating from a 16.5 mg/mL solution in chlorobenzene at 104 rad/s (1000 RPM) for 80 seconds, then placed in vacuum for 18 hours to remove additional solvent. The CYTOP 809-M dielectric layer was spin coated at 208 rad s$^{-1}$ (2000 RPM) for 60 s, then annealed at 55° C. overnight, yielding a 1.4 μm film.

Device Characterization and Threshold Voltage Extraction. Transistor characterization was carried out in a nitrogen environment in dark using an Agilent 4155 C Semiconductor Parameter Analyzer. Devices were tested immediately after fabrication, as well as after each radiation dose. The control sample was not irradiated but transported with and kept under similar environment as the irradiated samples. Capacitance measurements were taken using an Agilent E4980A LCR meter on irradiated samples. Threshold voltages were extracted from the square root of the drain current, $I_D$, with respect to the gate-source voltage, $V_{GS}$, using the maximum of the second derivative of $I_D$ with respect to $V_{GS}$ to bracket a linear extrapolation to where $I_D=0$ V, and that voltage taken as the threshold voltage.

X-ray Irradiation of diF-TES-ADT Radiation Sensors. X-ray radiation were administered to samples using a 6 MV Varian Clinac linear accelerator at a dose rate of 600 MU/min. The devices were sandwiched without compression between two slabs of tissue equivalent material, i.e. (Gammex) Solid Water® (top layer, to provide maximum percent depth dose to the devices, 1.5 cm thick; bottom layer, to provide backscatter to the devices, 10 cm thick) and irradiated through the layer in increments of 20 cGy from 0 cGy to 100 cGy, and then in increments of 200 cGy from 100 cGy to 1000 cGy. Test samples, which were approximately 1.5 cm×1.5 cm and contained arrays of OFET devices, were placed in the center of a 10×10 cm$^2$ field of 6 MV X-rays, 100 cm from the source at depth of 1.5 cm.

Mechanical Durability Testing of Flexible Dosimeters. Repeated bending of devices was accomplished via a computer-controlled servo to ensure a consistent curvature and the substrates were bent to a radius of 8 mm. Devices were electrically characterized for an irradiation dose of 100 cGy, before bending, and after each set of bending cycles, for sets of bending cycles from 1 to 10,000.

Chemical Analysis of irradiated diF-TES-ADT. Analysis of irradiated samples by gas chromatography/mass spectrometry (Bruker 436 GC/Scion SQ MS) showed diF TES ADT as the dominant product, along with trace amounts (<0.1%) of the monofluoro and trifluoro derivatives, in the same ratio as in the original un-irradiated sample. Proton NMR analysis of the irradiated sample (400 MHz Bruker Advance NEO) showed traces of endoperoxide, but this impurity often forms during sample preparation, and the same trace impurity was found when preparing pristine samples of diF TES ADT using the same conditions.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A radiation dosimeter comprising:
   an organic field effect transistor having composition and/or electronic structure exhibiting a shift in threshold voltage as a function of radiation dose, the organic field effect transistor including a single layer flexible backing;
   wherein organic semiconductor of the organic field effect transistor and human tissue receiving radiative treatment exhibit substantially matched mass attenuation coefficients for photon energies spanning at least two orders of magnitude.

2. The radiation dosimeter of claim 1, wherein the shift in threshold voltage after the radiation dose displays a positive regime when a magnitude of the radiation dose is less than 200 cGy, and wherein the shift in threshold voltage displays a negative regime when the magnitude of the radiation dose is greater than 200 cGy.

3. The radiation dosimeter of claim 2, wherein the positive shift in threshold voltage is associated with a decrease in hole trapping after receipt of the radiation dose.

4. The radiation dosimeter of claim 1, having sensitivity of 2-3·10$^7$ μC Gy$^{-1}$ cm$^{-3}$.

5. The radiation dosimeter of claim 1, wherein the photon energies span at least four orders of magnitude.

6. The radiation dosimeter of claim 1, wherein the mass attenuation coefficients of the organic semiconductor and human tissue are within 5 percent of one another.

7. The radiation dosimeter of claim 1 comprising an organic film of small molecule semiconductor in electrical communication with a source terminal and drain terminal.

8. The radiation dosimeter of claim 1, having thickness passing at least 95 percent of a radiation dose.

9. The radiation dosimeter of claim 1, wherein the organic field effect transistor is flexible.

10. The radiation dosimeter of claim 9, wherein the organic field effect transistor is operable to match one or more contours of the human body.

11. The radiation dosimeter of claim 9, wherein the organic field effect transistor exhibits a constant sensitivity to radiation doses for up to 10,000 bending cycles.

12. The radiation dosimeter of claim 1, wherein the flexible backing is configured for coupling the organic field effect transistor to skin of a patient.

13. A method of measuring a dose of radiation administered to a patient comprising:
positioning a radiation dosimeter over a target area for the radiation dose, the radiation dosimeter comprising an organic field effect transistor having composition and/or electronic structure exhibiting a shift in threshold voltage as a function of radiation dose, the organic field effect transistor including a single layer flexible backing, wherein organic semiconductor of the organic field effect transistor and human tissue receiving radiative treatment exhibit substantially matched mass attenuation coefficients for photon energies spanning at least two orders of magnitude;
passing the radiation dose through the radiation dosimeter to tissue of the target area; and
quantifying the dose of radiation from the shift in the threshold voltage of the organic field effect transistor in response to receiving the dose or radiation.

14. The method of claim 13, wherein the shift in threshold voltage after the radiation dose displays a positive regime when a magnitude of the radiation dose is less than 200 cGy, and wherein the shift in threshold voltage displays a negative regime when the magnitude of the radiation dose is greater than 200 cGy.

15. The method of claim 13, wherein the radiation dosimeter has sensitivity of $2\text{-}3\cdot 10^7$ $\mu C$ $Gy^{-1}$ $cm^{-3}$.

16. The method of claim 13, wherein the photon energies span at least four orders of magnitude.

17. The method of claim 13, wherein the mass attenuation coefficients of the organic semiconductor and human tissue are within 5 percent of one another.

18. The method of claim 13, wherein the organic field effect transistor is flexible.

19. The method of claim 18, wherein the organic field effect transistor is operable to match one or more contours of the human body.

* * * * *